United States Patent
Gomez et al.

(10) Patent No.: US 11,963,673 B1
(45) Date of Patent: Apr. 23, 2024

(54) LAPAROSCOPIC PORT CLOSURE AND NERVE BLOCK KIT

(71) Applicant: New Wave Endo-Surgery Inc., Coconut Creek, FL (US)

(72) Inventors: Ricardo Alexander Gomez, Lighthouse Point, FL (US); Sandy Lawrence Heck, Los Angeles, CA (US)

(73) Assignee: NEW WAVE ENDO-SURGICAL CORP., Coconut Creek, FL (US)

( * ) Notice: Subject to any disclaimer, the term of this patent is extended or adjusted under 35 U.S.C. 154(b) by 943 days.

(21) Appl. No.: 16/550,124

(22) Filed: Aug. 23, 2019

(51) Int. Cl.
| | |
|---|---|
| *A61B 17/00* | (2006.01) |
| *A61B 50/33* | (2016.01) |
| *A61F 15/00* | (2006.01) |
| *A61M 19/00* | (2006.01) |

(52) U.S. Cl.
CPC .......... *A61B 17/0057* (2013.01); *A61B 50/33* (2016.02); *A61F 15/001* (2013.01); *A61M 19/00* (2013.01); *A61B 2017/00637* (2013.01)

(58) Field of Classification Search
CPC ....... A61M 19/00; A61F 15/001; A61F 15/00; A61B 2017/00637; A61B 50/33; A61B 17/0057; A61B 2017/00353; A61B 17/04; A61B 17/06
USPC ................................................. 206/571, 223
See application file for complete search history.

(56) References Cited

U.S. PATENT DOCUMENTS

| | | | | |
|---|---|---|---|---|
| 3,851,649 A | * | 12/1974 | Villari | A61B 50/30 206/223 |
| 4,522,302 A | * | 6/1985 | Paikoff | A61M 5/003 206/570 |
| 5,318,543 A | * | 6/1994 | Ross | A61J 15/0023 604/170.01 |
| 5,453,094 A | * | 9/1995 | Metcalf | A61B 17/3417 206/571 |
| 6,910,581 B2 | * | 6/2005 | McMichael | A61B 50/33 206/370 |
| 2004/0004019 A1 | * | 1/2004 | Busch | A61B 50/30 206/370 |
| 2004/0031721 A1 | * | 2/2004 | Mann | A61B 10/04 206/570 |
| 2009/0194453 A1 | * | 8/2009 | Thorne, Jr. | A61J 1/2096 206/571 |
| 2015/0114864 A1 | * | 4/2015 | Hartfelder | A61B 34/20 206/370 |
| 2019/0083199 A1 | * | 3/2019 | Cassinis | A61B 50/33 |

FOREIGN PATENT DOCUMENTS

WO    WO-9609796 A2 * 4/1996 ......... A61B 17/0469

* cited by examiner

*Primary Examiner* — Rafael A Ortiz
(74) *Attorney, Agent, or Firm* — Grogan, Tuccillo & Vanderleeden, LLP

(57) ABSTRACT

The present invention relates to a sterilized packaging kit having surgical components used in a combined laparoscopic port closure procedure and targeted nerve block delivery that can both be performed by a surgeon. The specialized kit allows the surgeon to perform both a pre-op or post op nerve block and port closure.

11 Claims, 4 Drawing Sheets

LAPAROSCOPIC PORT CLOSURE AND NERVE BLOCK KIT

FIELD OF THE INVENTION

The present invention relates generally to a sterile packaging kit having surgical components to be used in a combined laparoscopic port closure procedure and targeted anesthesia delivery during a laparoscopic procedure.

BACKGROUND OF THE INVENTION

Laparoscopic Surgery also referred to as minimally invasive surgery is a surgical procedure whereby medical instruments are introduced through an opening in the percutaneous surface and directed into the internal cavity area of a patient. Several small incisions are made, and with the use of a specialized camera called a laparoscope, visualization takes place. Depending on the type of surgery performed specialized tools are needed. Laparoscopy has advanced much in the last 3 decades, but some basic problems still remain unaddressed and continue to challenge surgeons today. Surgeons still struggle to safely close their laparoscopic ports. Despite the promise of minimally invasive surgery, patients continue to suffer postop pain and surgeons continue to rely on opioids for pain control. Another problem is the failure to properly close laparoscopic ports which can lead to hernias in up to 8% of all cases. These are dangerous life-threatening complications that require expensive and often emergent reoperation that may not necessarily be reimbursed by the insurance companies. Hernias are a persistent problem in laparoscopy because it is challenging to safely close the deep tissue layers through small laparoscopic skin incisions. The obesity epidemic has made it even more difficult for surgeons to suture the deep fascial layer. Surgeons used to skip closing difficult port sites, but standards of care now require all ports greater than 10-12 mm to be closed. The problem being that current solutions are costly, ineffective and sometimes dangerous.

Although small laparoscopic incisions result in less pain than traditional open surgery, they still require a means of pain control. And since these patients are expected to recover and leave the hospital quickly, surgeons have traditionally rallied on IV and prescription opiates to control pain. Research has revealed that as many as 1 in 12 surgical patients develop an opiate addition that started with their pain pills. When it comes to pain control, laparoscopic surgeons are similarly challenged. They are challenged because no easy solutions exist, and surgeons still rely on opiates in nearly every surgery. While opiates are prescribed to relieve acute pain, the problem is that prolonged use can lead to opiate addiction and abuse. If not controlled, opiate misuse and an addiction can lead to death from overdose. Opioid addiction was the leading cause of drug overdose in 2017 in the United States.

The opiate crisis is a problem in every community across the US, and surgeons and hospitals are trying to move away from opioids as quickly as possible, but few other solutions are available for post-op pain. One of the most effective methods for opioid-free pain control is an abdominal wall nerve block, which involves injecting a local anesthetic directly into a nerve layer.

Unfortunately, this procedure is not easily performed. The nerve layer is small and dangerously close to abdominal organs. So, providers often need ultrasound guidance to deliver the nerve block. But this adds delays and costs, and is therefore rarely performed in laparoscopic or robotic surgeries. Some surgeries have resorted to doing these blocks blindly but the inaccuracy and danger of the technique has most providers looking for a better solution. Improved pain control is more than just about reducing opioid use. A patient's perception of how well a surgery went is strongly related to the pain and discomfort they feel postop. Reducing pain improves patient satisfaction, and better pain control has benefits for the hospital too. Since patient can ambulate sooner, they can also be discharged sooner, and can avoid the constipation and other side effects of opioids further speeding their recover and readiness for discharge.

There is a need in the field for a device that can help dramatically reduce the use of opioids in laparoscopic surgical procedures.

SUMMARY OF THE INVENTION

The present invention is the first and only combined port site nerve block needle kit and port closure device. It allows surgeons to bilaterally inject, directly, and with precision, into the peritoneal nerve layer without ultrasound guidance, without delays, and without the task of inadvertent injuring the patient.

In the field of Laparoscopic surgery, a series of different procedures are performed that in combination result in a successful surgery. Abdominal wall nerve blocks have been shown to reduce opioid use by over 60%, and in many cases can eliminate the need for opioids entirely. Studies show that over 70% of patients receiving abdominal wall nerve blocks are pain free within an hour, resulting in the patients being discharged significantly earlier. Since every cc of anesthetic is injected directly into the nerve plane, very little is lost in surrounding tissues compared to local infiltration. This is especially important when injecting expensive long-acting local anesthetics.

In its preferred embodiment, the port closure device would provide a mechanically controlled, gold standard closure that meets the gold standard guidelines of the Jonsson-Israelsson rule of fascial closure, with suture bites that are 1 cm symmetrical around the edge of the defect, and with a knot just above the fascial plane. The present port closure device performs this task with mechanical precision by incorporating two integrated needles that simultaneously hit both edges of the fascial defect with the push of a button. This ensures that the suture bites are exactly 180 degrees across from each other, something difficult to achieve with any other port closure device. It makes closing ports quick and eliminates variability between users.

Ideally it would be beneficial to just have one kit with the correct medical instruments for a desired procedure. This would minimize the repetition of similar tools, and shorten the time it takes to perform a procedure. The efficiency gained by combining these two procedures together is significant, since the same deep abdominal wall tissue layers need to be accessed for both port closure and nerve blocking. Combining the procedures means that the surgeon only needs to find and identify the layer once. And using a combined targeted anesthesia delivery device with a port closure device provides a means of consistently performing the combined procedures.

The port closure nerve block kit comes with the laparoscopic nerve block needle to deliver anesthesia separately or in conjunction with the port block device. By using the peritoneal reference plane established by the port closure device, the needles can be guided to the correct location for the nerve block. In its preferred embodiment, it is a 19-gauge needle with a specialized blunt tip ideal for laparoscopically assisted placement and an ergonomic handle for superior control. It may also include a set of injection tubing and syringe. The kit also includes antimicrobial port site wound dressings, which are shaped and sized for laparoscopic incisions, and can include multiple sizes for varying port diameters, and can include antibacterial properties to help promote healing.

In the case of the present invention there is provided for the first time, a sterilized self-contained kit comprising a laparoscopic port closure device, a sterilized anesthetic needle to deliver a nerve block, and bandage kit.

DESCRIPTION OF DRAWINGS

The preferred embodiments of the invention will hereinafter be described in conjunction with the appended drawings provided to illustrate and not to limit the invention in rigidity to instrument devices the invention is not limited to the embodiments illustrated in the drawings but are merely used to illustrate the wide variety of uses of this invention. Therefore, the foregoing is considered as illustrative only of the principles of the invention. Since numerous modification and changes will readily occur by those skilled in the art, it is not desired to limit the invention to the exact construction and operation shown and described and accordingly, all suitable modifications and equivalents may be resorted to, falling within the scope of the invention.

Figure 2:
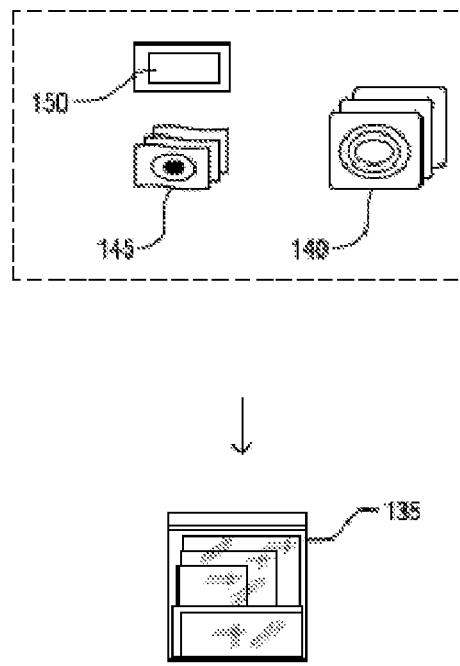

In regards to FIG. 2 a perspective view of an exemplary embodiment of a bandage kit having sterilized gauzes and assorted bandages.

Figure 3:
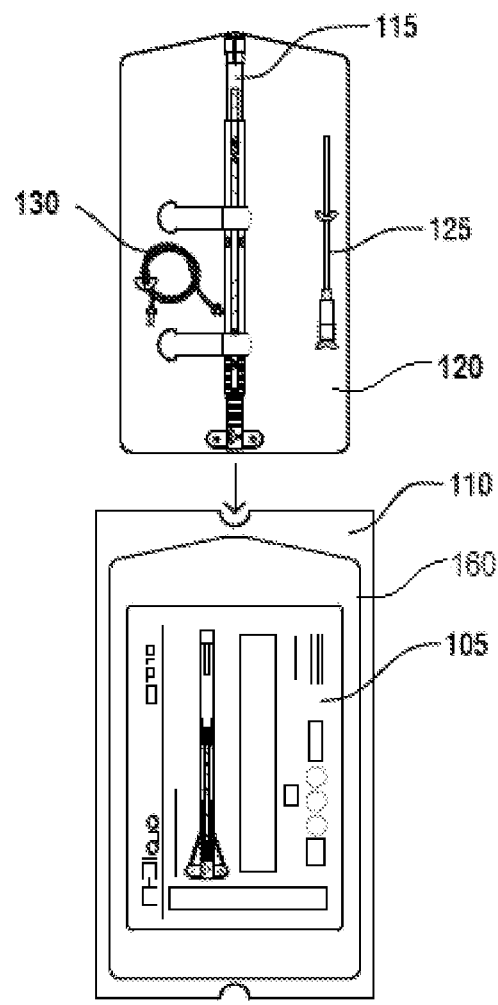

In regards to FIG. 3 a perspective view of an exemplary embodiment of the tray package including members of the kit.

Figure 4:
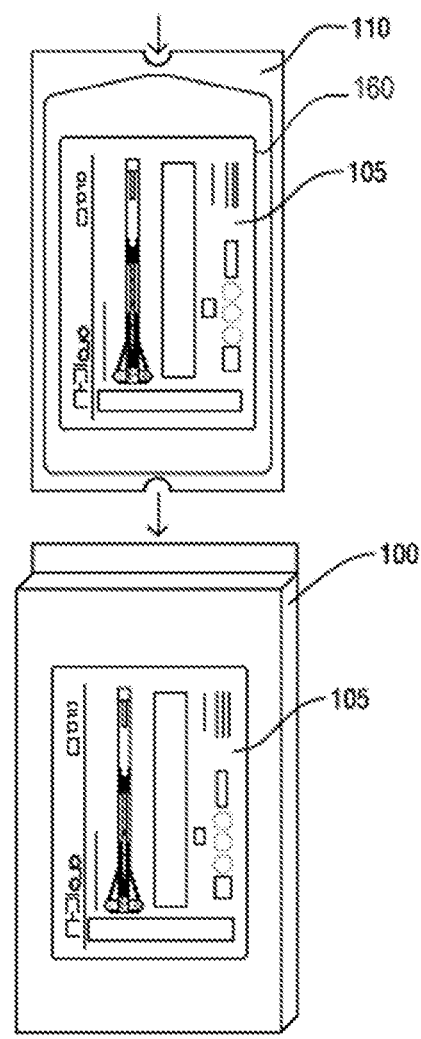

In regards to FIG. 4 a perspective view of an exemplary embodiment of the tray package inserted into a sealed pouch with all members of the kit prepositioned before being stored into a specialized kit box.

While the various features of this invention are hereinafter described and illustrated as being particularly adapted for providing rigidity to instrument devices the invention is not limited to the embodiments illustrated in the drawings but are merely used to illustrate the wide variety of uses of this invention. Therefore, the foregoing is considered as illustrative only of the principles of the invention. Since numerous modification and changes will readily occur by those skilled in the art, it is not desired to limit the invention to the exact construction and operation shown and described and accordingly, all suitable modifications and equivalents may be resorted to, falling within the scope of the invention.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise. While the various features of this invention are hereinafter described and illustrated as being particularly adapted for providing rigidity to instrument devices the invention is not limited to the embodiments illustrated in the drawings but are merely used to illustrate the wide variety of uses of this invention. Therefore, the foregoing is considered as illustrative only of the principles of the invention. Since numerous modification and changes will readily occur by those skilled in the art, it is not desired to limit the invention to the exact construction and operation shown and described and accordingly, all suitable modifications and equivalents may be resorted to, falling within the scope of the invention.

Figure 1:
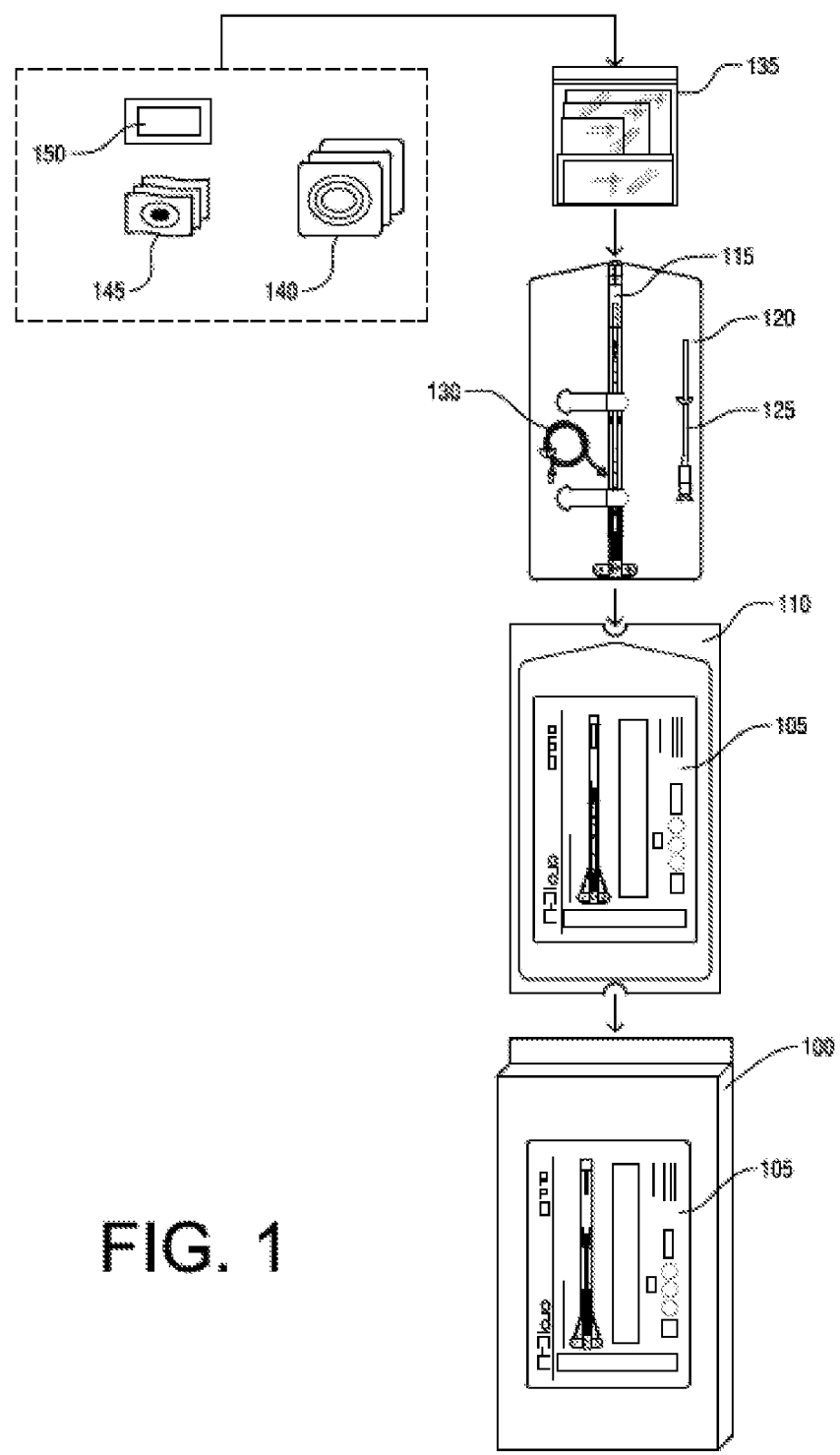
FIG. 1 provides a perspective view of an exemplary embodiment of a sterilized advanced laparoscopic port closure kit components and targeted anesthesia delivery system components used in laparoscopic procedures.

With regards to FIG. 1 a perspective view of an exemplary embodiment of a sterilized advanced laparoscopic port closure kit components and targeted anesthesia delivery system is displayed. They are typically used in laparoscopic surgery. The invention comprises an assembled kit containing the necessary supplies for performing a port closure and or nerve block procedure. It will typically be performed in an operating room setting or at a healthcare facility under the supervision of a medical professional. The kit has four separate sections. The sections are comprised of a shipping box (100) containing a kit pouch, a (110) Lift tray (120), and a bandage kit all assembled. The kit box (100) is in the form of a rectangle box made out of cardboard paper, and a kit label (105). An assortment of large Island bandages (140), smaller assorted bandages (145) and sterilized absorbent pads (150) are inserted into a flexible self-sealing plastic bag (135), they form part of another section of the kit. The self-sealing plastic bag is also referred to as the bandage kit (135). The bandage kit is ten inserted into the kit pouch (110) along with the lift tray (120). These sections are sealed to maintain sterility of the components. Assembling the sections in this manner allows quick use by the health care professional.

In regards to FIG. 2 a perspective view of an exemplary embodiment of a bandage kit having sterilized gauzes (150) and assorted bandages. Sterilized absorbent pads (150), smaller assorted bandages (145) large island bandages (140) are inserted into a bandage kit bag (135). The bandage kit can be self-sealing.

In regards to FIG. 3 a perspective view of an exemplary embodiment of the tray package includes members of the kit. The port closure device (115) is attached to a paper board lift tray (120) that holds the specialized tubing (130), and a targeted anesthesia delivery apparatus in the form of a nerve block device (125). The outer peel pouch (160) is made of a transparent flexible plastic sheet bonded about its perimeter to a backing sheet, which may be made out of a gas permeable material preferably made out of a non-woven, spun bond olefin such as is sold under the trademark Tyvek™ by the Dupont Corporation of Wilmington, Del. Once the components are assembled and sealed, they are prepared for the final section.

In regards to FIG. 4 a perspective view of an exemplary embodiment of the tray package (110) inserted into a sealed pouch with all members of the kit prepositioned and entered into the Kit box (100).

It should be noted that anesthesiologist do not perform port closure procedures, but instead, prior to surgery may perform nerve block procedures. Surgeons on the other hand can perform nerve block procedures but because of the difficulty in accurately reaching the rectus sheath often defer to the anesthesiologist. The present invention solves a problem in the field by allowing surgeons to reliably perform a nerve block in combination with a port closure procedure. Studies in pain reduction have shown that the greatest benefit to the patients occurs when a nerve block is delivered closest to completion of a surgery. This has the benefit of providing the most effective pain reduction for the patient without the disadvantages associated with using larger amounts of opioids.

The present application consists of a kit for use during laparoscopic surgical procedures comprising at least a port closure device and a targeted anesthesia delivery apparatus packaged in a sterile manner for single use and disposal. The kit comprises a sterile, resealable bandage kit, wherein the bandage kit includes a plurality of bandage types therein. Wherein items of the kit are positioned in a sterile tray. Wherein the tray of the kit is inserted into a sealed sterile pouch, wherein the pouch is inserted into a specialized kit box.

The invention claimed is:

1. A kit for use during laparoscopic surgical procedures, comprising:
   a combined port closure device and targeted anesthesia delivery apparatus packaged in a sterile manner for single use and disposal;
   wherein the combined port closure device and targeted anesthesia delivery apparatus is configured for use first in delivering anesthesia to a patient, and second for use in closing a laparoscopic port in the patient;
   wherein the combined port closure device and targeted anesthesia delivery device has two integrated needles, at least one of which is used for delivering the anesthesia to the patient, and that are thereafter configured to contact both edges of a fascial defect with the push of a button of the combined port closure device and targeted anesthesia delivery apparatus to provide suture bites that are 180 degrees across from each other when closing the laparoscopic port;
   wherein the port closure device and the targeted anesthesia delivery apparatus packaged in the kit are configured for a desired laparoscopic surgical procedure.

2. The kit of claim 1 further comprising a sterile, resealable bandage kit.

3. The kit of claim 2 wherein the bandage kit includes a plurality of bandage types therein.

4. The kit of claim 2 wherein items of the kit are positioned in a sterile tray.

5. The kit of claim 3 wherein the tray is inserted into a sealed sterile pouch.

6. The kit of claim 4 wherein the pouch is inserted into a specialized kit box.

7. The kit of claim 1, wherein:
   the combined port closure device and targeted anesthesia delivery apparatus is configured for use in delivering the anesthesia to the patient, and then to provide suture bites that are 180 degrees across from each other when closing the laparoscopic port, without removing the combined port closure device and the target anesthesia delivery apparatus from the laparoscopic port.

8. A kit used by a surgeon during laparoscopic surgical procedures, comprising:
   a combined port closure device and targeted anesthesia delivery apparatus packaged in a sterile manner for single use and disposal, and a sterile resealable bandage kit,
   wherein the combined port closure device and targeted anesthesia delivery apparatus is configured for use in delivering anesthesia to a patient
   and for use in closing a laparoscopic port in the patient and includes two integrated needles; and
   wherein the items of the kit are positioned in a sterile tray and the sterile tray is inserted into a sealed sterile pouch.

9. The kit of claim 8 wherein the bandage kit includes a plurality of bandage types therein.

10. The kit of claim 8 wherein the pouch is inserted into a specialized kit box.

11. A kit configured for use by a surgeon during a laparoscopic surgical procedure, comprising:
    a sealed, sterile pouch containing a tray, a combined port closure device and targeted anesthesia delivery apparatus attached to the tray, and a coil of tubing supported by the tray, the tray including an outer peel pouch sealingly enclosing the combined port closure device and targeted anesthesia delivery apparatus, and the coil of tubing;
    a self-sealing bag containing sterilized gauzes and a plurality of assorted bandages and/or pads; and
    a box enclosing the sealed, sterile pouch and the self-sealing bag, the box having a label identifying contents of the box;
    wherein the combined port closure device and targeted anesthesia delivery apparatus is configured for use in delivering anesthesia to a patient and
    for use in closing a laparoscopic port in the patient via sutures, the anesthesia delivery and port closure occurring without necessitating removal of the combined port closure device and targeted anesthesia delivery apparatus from the laparoscopic port between anesthesia delivery and port closure procedures.

* * * * *